United States Patent
Bhullar et al.

(10) Patent No.: US 6,562,210 B1
(45) Date of Patent: May 13, 2003

(54) CELL FOR ELECTROCHEMICAL ANAYLSIS OF A SAMPLE

(75) Inventors: Raghbir Singh Bhullar, Indianapolis, IN (US); Douglas P. Walling, Indianapolis, IN (US); Brian Hill, Indianapolis, IN (US)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/475,904

(22) Filed: Dec. 30, 1999

(51) Int. Cl.⁷ .................................. G01N 27/327
(52) U.S. Cl. ..................... 204/403.03; 204/403.04; 204/403.02
(58) Field of Search ................. 204/403.02, 403.03, 204/403.04, 403.1, 403.11, 403.12, 409

(56) References Cited

U.S. PATENT DOCUMENTS

| | | |
|---|---|---|
| 4,161,437 A | 7/1979 | Fleckenstein |
| 4,829,003 A | 5/1989 | Arney, Jr. |
| 4,938,860 A | 7/1990 | Wogoman |
| 5,030,310 A | 7/1991 | Wogoman |
| 5,128,015 A | 7/1992 | Szuminsky et al. |
| 5,264,103 A * | 11/1993 | Yoshioka et al. ........ 204/403.1 |
| 5,352,352 A | 10/1994 | Tsukada et al. |
| 5,437,999 A * | 8/1995 | Diebold et al. ......... 204/403.11 |
| 5,723,345 A * | 3/1998 | Yamauchi et al. ........... 204/400 |
| 5,779,867 A * | 7/1998 | Shieh .................... 204/403.12 |
| 5,909,114 A | 6/1999 | Uchiyama et al. |
| 5,916,156 A | 6/1999 | Hildenbrand et al. |
| 6,156,173 A * | 12/2000 | Gotoh et al. ........... 204/403.04 |
| 6,168,699 B1 * | 1/2001 | Frenkel et al. ......... 204/403.11 |

FOREIGN PATENT DOCUMENTS

JP 57-156564 9/1982

* cited by examiner

Primary Examiner—Robert J. Warden, Sr.
Assistant Examiner—Kaj K. Olsen
(74) Attorney, Agent, or Firm—Brinks Hofer Gilson & Lione

(57) ABSTRACT

According to an aspect of the invention, an electrochemical cell for analysis of a sample is provided, comprising a dual electrode having a dielectric strip with electrical conductors on opposite sides. According to a preferred embodiment, the electrochemical cell comprises a base, and a first reagent the proximate the dual electrode. According to a further preferred embodiment, a second reagent is provided proximate the dual electrode. A cover may also be provided comprising a sample aperture. According to a particularly preferred embodiment, the first and second reagents are superposed, and the dual electrode is between the first and second reagents. The dual electrode separates the two and preserves chemical stability until a sample is applied.

14 Claims, 6 Drawing Sheets

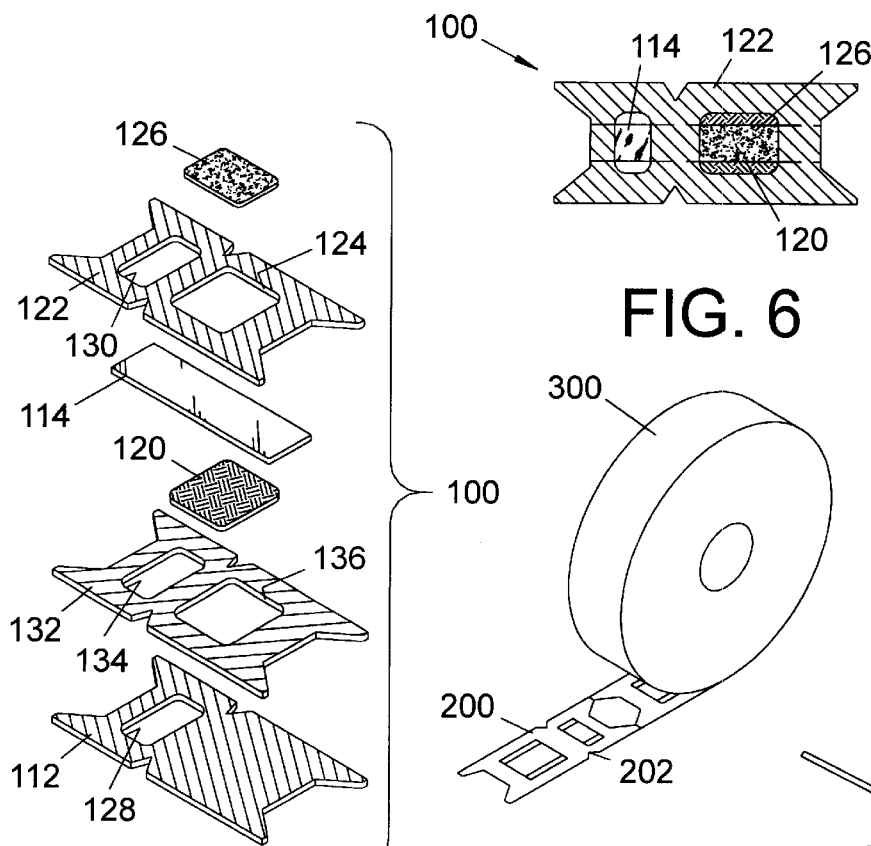
FIG. 6
FIG. 5
FIG. 8
FIG. 15
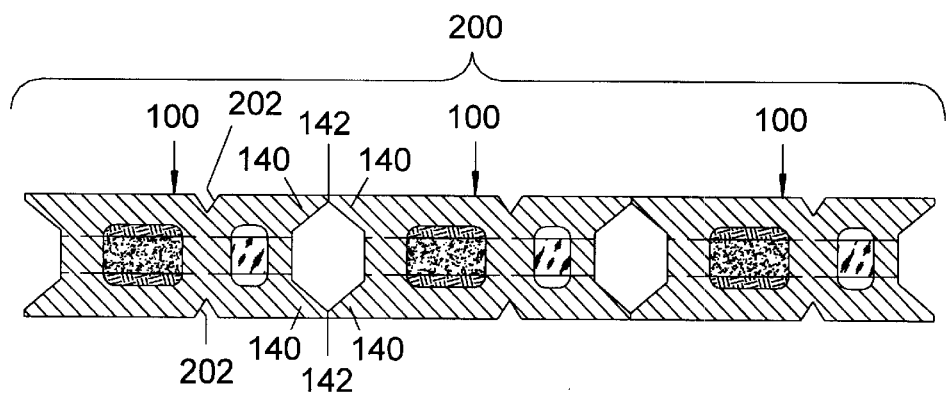
FIG. 7

CELL FOR ELECTROCHEMICAL ANAYLSIS OF A SAMPLE

BACKGROUND OF THE INVENTION

The present invention relates to cells for electrochemical analysis.

Cells for electrochemical analysis are well known. They have been used to determine the concentration of various analytes from biological samples, particularly from blood. Cells for electrochemical analysis are described in U.S. Pat. Nos. 5,413,690; 5,762,770 and 5,798,031; as well as in International Publication No. WO99/13101, each of which are hereby incorporated by reference.

A cell for electrochemical analysis typically includes a sensor strip. The sensor strip includes a space that holds the sample to be analyzed, may include reagents to be released into the sample, and includes an electrode set. The electrode set normally includes an insulating substrate, and electrodes that contact the sample, which have contact pads for electrically connecting the electrodes to the electronics of an electrochemical biosensor.

SUMMARY OF THE INVENTION

According to an aspect of the invention, a cell for electrochemical analysis of a liquid sample is provided, comprising a base, a dielectric strip having opposing first and second surfaces, on the base and defining a gap therebetween, a first electrical conductor on the first surface that defines a first sensing region over the gap, a electrical conductor on the second surface that defines a second sensing second region opposite the first sensing region.

According to a further aspect of the invention, a cell for electrochemical analysis of a liquid sample is provided, comprising a base, a dielectric strip having opposing first and second surfaces, on the base and defining a gap therebetween, a first electrical conductor on the first surface, a second electrical conductor on the second surface, wherein the first electrical conductor does not extend beyond the first surface, and the second electrical conductor does not extend beyond the second surface.

According to a still further aspect of the invention, an electrochemical cell for analysis is provided, comprising a base, a first reagent on the base, an electrode set on the base comprising a strip formed from a dielectric material, the strip having a first face with a first electrical conductor on the first face and having a second face opposite the first face with a second electrical conductor on the second face, a second reagent on the base, the first and second reagents being superposed with the electrode set in between, and a cover on the base overlaying the electrode set, the cover comprising a sample aperture superposed on the first and second reagents.

According to a still further aspect of the invention, a method of making an electrochemical cell for analysis is provided, comprising integrating a base, an electrode set on the base, and a first reagent on the base proximate the dual electrode, the electrode set comprising plastic strip metallized on opposite sides.

According to a still further aspect of the invention, a method of making an electrochemical cell for analysis is provided, comprising integrating a base, a first reagent on the base, an electrode set on the base comprising a plastic strip metallized on opposite sides, a second reagent on the base, the first and second reagents being superposed with the electrode set in between, and a cover on the base, the cover comprising a sample aperture superposed on the first and second reagents.

Many fluid samples may be analyzed according to the numerous aspects of the invention. For example, human body fluids such as whole blood, blood serum, urine, and cerebrospinal fluid may be measured. Also fermentation products and environmental substances, which potentially contain environmental contaminants, may be measured.

BRIEF DESCRIPTION OF THE DRAWINGS

FIG. 5 presents an exploded perspective view of a cell for electrochemical analysis according to a further aspect of the invention.

FIG. 6 presents a top plan view of the FIG. 5 cell.

FIG. 7 presents a top plan view of a plurality of cells connected in seriatim as a strip, according to a further aspect of the invention.

FIG. 8 presents a rolled strip of cells, according to a further aspect of the invention.

FIG. 15 presents a side view of a strip of sensors packaged in a fanfold arrangement, according to a further aspect of the invention.

DETAILED DESCRIPTION

Figure 1:
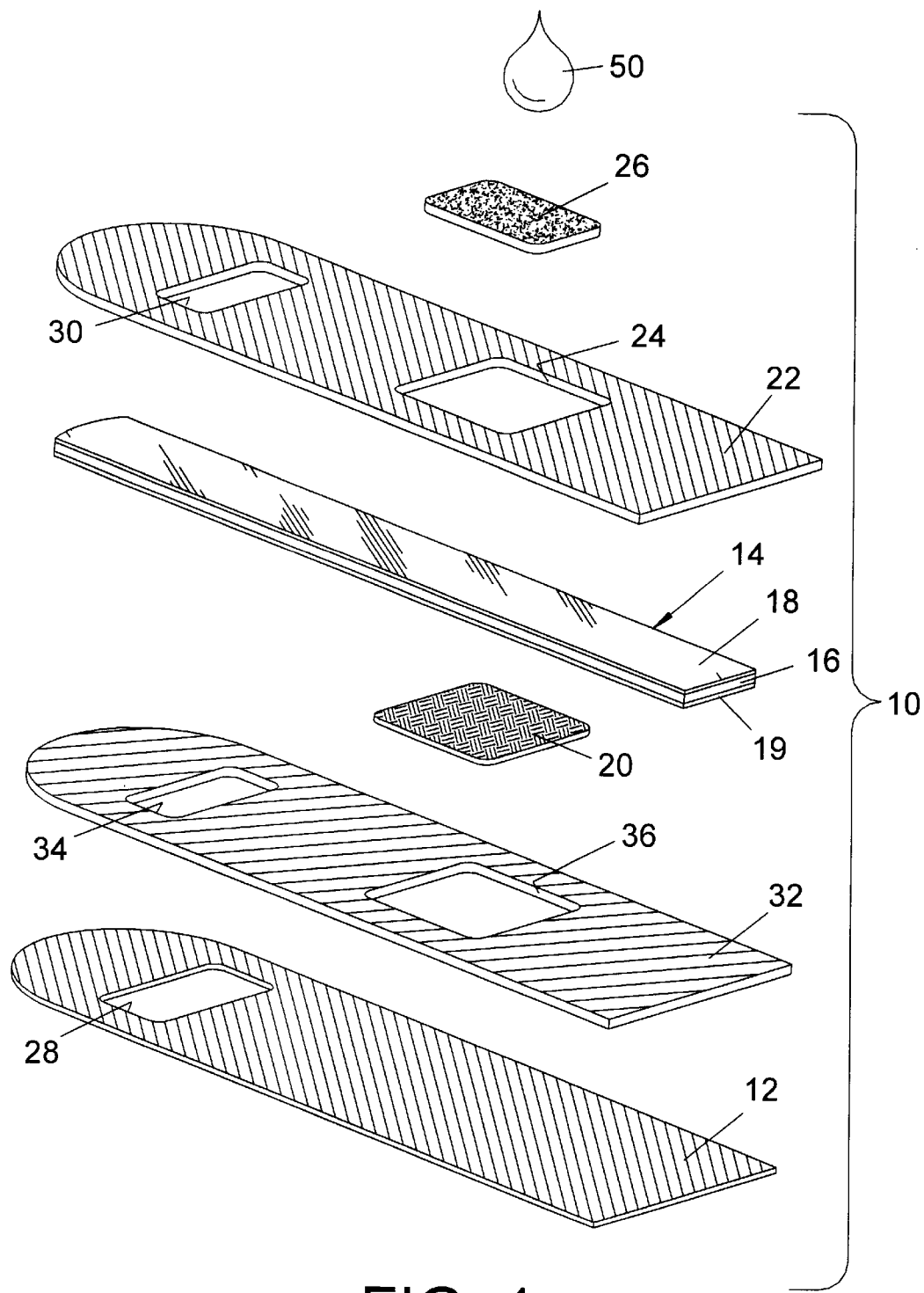
FIG. 1 presents an exploded perspective view of a cell for electrochemical analysis according to an aspect of the invention.

Various aspects of the invention are presented in FIGS. 1–14, which are not drawn to scale and wherein like components in the several views are numbered alike. Referring now specifically to FIG. 1, an exploded perspective view of an exemplary embodiment of a cell 10 for electrochemical analysis for analysis of a sample is presented. The cell 10 for electrochemical analysis comprises a base 12, and an electrode set 14 comprising a strip 16 formed from a dielectric material. The strip 16 has a first face with a first electrical conductor 18 on the first face and a second face opposite the first face with a second electrical conductor 19 on the second face. The base 12 and electrode set 14 are configured so that a liquid sample 50 applied to the cell 10 contacts the first and second faces of the strip 16 whereby an electrochemical property of the sample 50 can be measured.

The areas of the first and second electrical conductors 18 and 19 where the sample 50 contacts, and where the electrochemical reaction takes place, are defined herein as the first and second sensing regions. According to an aspect of the invention, the first and second sensing regions face in opposite directions. In the exemplary embodiments presented herein, the first and second sensing regions face in opposite directions due to the first and second electrical conductors 18 and 19 being on opposite faces of the dielectric strip 16 separating the two. According to a preferred embodiment, the first and second electrical conductors 18 and 19 do not extend beyond the dielectric strip 16.

The first and second electrical conductors 18 and 19 may be formed from any electrically conductive material suitable for use in an electrode for electrochemical analysis, including metal, carbon, and conductive paints. Suitable conductive paints include silver and/or carbon containing paint, particularly graphite. Such materials are available from Atcheson Colloids, Inc. of Michigan, U.S.A., and other suppliers. Examples of metals that may be implemented in forming the electrodes 18 and 19 include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and oxides, alloys or metallic compounds of these elements. Preferably, the electrode set is constructed of gold, platinum, palladium, iridium, or alloys of these metals, since such noble metals and their alloys are unreactive in biological systems.

Figure 2:
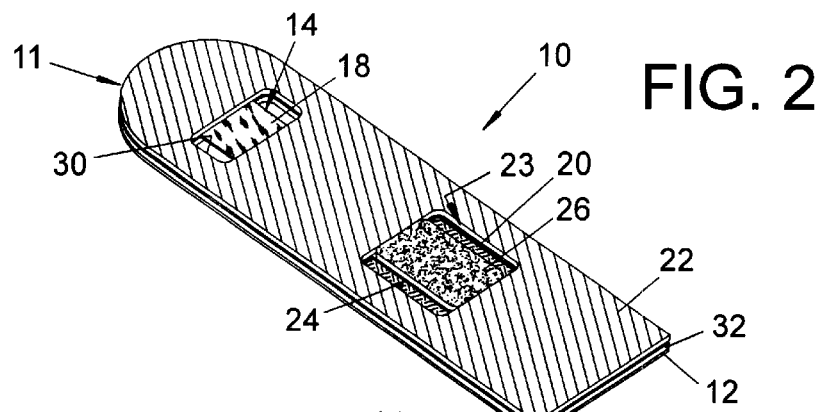
FIG. 2 presents a perspective view of the top of the FIG. 1 cell.
Figure 3:
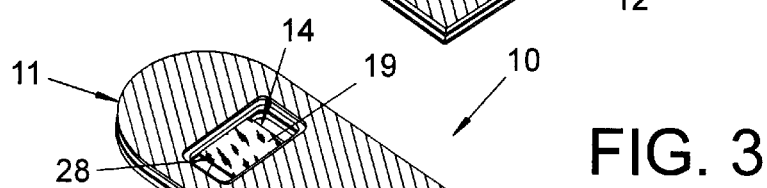
FIG. 3 presents a perspective view of the bottom of the FIG. 1 cell.
Figure 4:
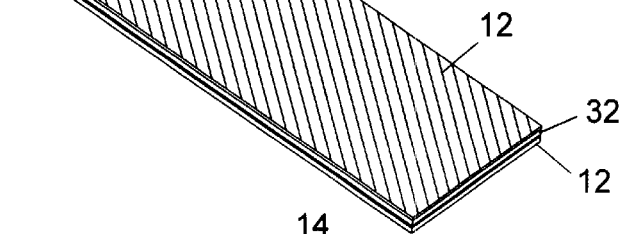
FIG. 4 presents a perspective view of the top FIG. 1 cell with partial cross-sections.

Referring now to FIGS. 2, 3 and 4, additional perspective views of the cell 10 for electrochemical analysis are presented. FIG. 2 provides a top perspective view of the cell 10, FIG. 3 presents a bottom perspective view of the cell 10, and FIG. 4 presents a top perspective view with a partial cross section of the cell 10. The numerous components already described in relation to FIG. 1 are presented again in FIGS. 2–4.

In the example presented in FIGS. 1–4, the cell 10 comprises a base 12, a spacer 32 on the base 12, and a cover 22 on the spacer 32. A first reagent 20 may be provided on the base 12 proximate the electrode set 14, and may be deposited directly on the base 12. The electrical conductors 18 and 19 on either side of the plastic strip 16 are electrically isolated from each other by the dielectric strip 16. The cell 10 for electrochemical analysis may comprise a plurality of electrode sets 14. The base 12, cover 22, and spacer 32 are preferably formed from a dielectric material, such as a plastic. The cover 22 may be formed from a printable substance screen printed onto the base 12 and/or spacer 32.

In use, an electrical potential difference is applied across the electrical conductors 18 and 19, and the sample 50 is placed on the electrode set 14 over the first reagent 20. An electrochemical reaction commences, particularly along the edges of the electrode set 14, that is indicative of a chemical property of the sample. The indication may be in the form of a current, an impedance, or other measurement, as is known in the art.

Placing the first and second electrical conductors 18 and 19 close together is advantageous as closer proximity tends to decrease the time it takes to make a measurement. An electrical coating on both sides the strip 16 provides a close proximity with reproducibility, minimum variation, and minimum cost. The electrical conductors 18 and 19 may comprise electrical foil adhered to the strip 16, or the strip 16 may be metallized, for example by plating or sputtering. The strip 16 is preferably plastic.

Still referring to FIGS. 1–4, the spacer 32 overlies the base 12 to separate the electrode set 14 from the base 12. The spacer 32 preferably includes an aperture 36 to thereby provide a gap (best shown in FIG. 12) between one side of the strip 16 and the base 12. The cover 22 overlies the electrode set 14 and preferably includes an aperture 24 overlaying and having similar shape and size as the aperture 36 in the spacer 32 to thus provide a well 23 to receive the sample 50. The cover 22 may be formed from a hydrophobic material to assist in confining the sample to the well 23.

Figure 12:
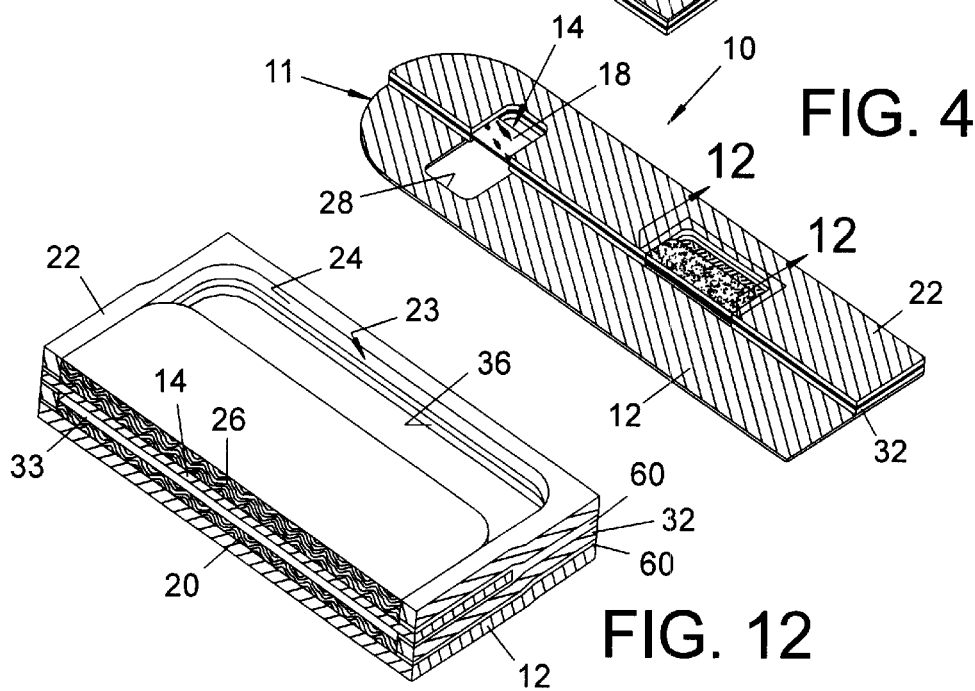
FIG. 12 presents an enlarged cross sectional view of the area indicated as 12—12 of FIG. 4.

The electrode set 14 is preferably suspended in the well 23. As best shown in FIG. 12, an enlarged view of the area indicated as 12—12 of FIG. 4, the spacer 32 separates the electrode set 14 from the base 12 and defines a space 33 therebetween within the well 23. The space 33 between the strip 16 and the base 12 preferably acts as a capillary channel. This ensures that the oppositely facing active regions of the electrical conductors 18 and 19 are fully contacted with the sample 50. Additional capillary channels may be formed in the electrode set 14.

Referring again to FIGS. 1–4, a second reagent 26 may be provided on the base 12 proximate the electrode set 14, and may be deposited directly on the exposed surface of the first electrical conductor 18 within the aperture 24. The first and second reagents 20 and 26 may be superposed with the electrode set 14 in between. This arrangement greatly increases chemical stability of the two reagents 20 and 26 since they are physically separated by the electrode set 14. Optimum electrical contact with both reagents is provided by the oppositely facing electrical conductors 18 and 19 of the electrode set 14. Thus, the electrode set 14 performs at least two functions: electrical contact for sample analysis, and separating the reagents prior to sample analysis. The electrode set 14 may be perforated to facilitate contact of the two reagents 20 and 26 after application of the sample 50.

Still referring to FIGS. 1–4, the first and second reagents 20 and 26 are preferably superposed with the dual electrode in between. The sample aperture 24 in the cover 22 is superposed on the first and second reagents 20 and 26. This stacked arrangement conveniently places all the analytical components in a single location on the base 12 where a sample to be analyzed is applied in liquid form.

According to a further preferred embodiment, the base 12 includes an aperture 28, the spacer 32 includes a second aperture 34 overlaying the aperture 28 in the base 12, and the cover 22 comprises a second aperture 30 overlaying the aperture 28 in the base 12 and second aperture 34 in the spacer 32 to thereby provide access to both sides of the electrode set 14. An electrical connector (not shown) of an analysis unit (not shown) may be connected to both sides of the electrode set 14. A simple spring loaded clip type connector, for example, may be implemented. A variety of connectors may be suitable for use with the cell 10 for electrochemical analysis.

Referring now to FIGS. 5 and 6, a perspective view and top plan view, respectively, of a cell 100 for electrochemical analysis is presented according to a further aspect of the invention. The cell 100 for electrochemical analysis comprises a base 112, and an electrode set 114 on the base 112. The electrode set 114 comprises a strip of dielectric material having a first face with an electrical conductor applied thereto and a second face opposite the first face with a second electrical conductor applied thereto, as previously described in relation to electrode set 14.

A first reagent 120 is on the base 112 proximate the electrode set 114. A cover 122 is provided on the base 112, and comprises an aperture 124. A second reagent 126 is provided on the base 112 proximate the electrode set 114. The first and second reagents 120 and 126 are superposed with the electrode set 114 in between. The aperture 124 is superposed on the first and second reagents 120 and 126.

One spacer 132 is provided directly on the base 112, and the electrode set 114 is between the spacer 132 and the cover 122. The base 112 comprises an aperture 128 and the cover 122 comprises a second aperture 130 superposed, as shown, over the aperture 128 in the base 112. The spacer 132 has an aperture 136 and a second aperture 134 corresponding with the apertures 130 and 124 in the cover 122.

Referring now to FIG. 7, a strip 200 is presented comprising a plurality of cells 100 for electrochemical analysis connected in seriatim, according to a further aspect of the invention. Each cell 100 is provided with an opposing pair of legs 140 on each end that may be connected. The legs 140 of adjacent cells 100 may be scored where they join, as indicated at 142, to assist in pulling them apart before or after use.

Referring now to FIG. 8, a further aspect of the invention is presented wherein the strip 200 is arranged as a roll 300. Referring now to FIG. 15, the strip 200 may be folded back and forth onto itself in a fanfold arrangement 400. Alternatively, the individual cells 100 may be separated and stacked, or removably applied to backing sheets or strips that are, in turn, stacked, folded, coiled, or any other of the innumerable packaging variations possible.

Referring again to FIG. 8, the edges of the sensors 100 may be provided with notches 202 along the edges. The notches increase flexibility in the longitudinal direction of the strip, and may be implemented when the strip 200 is rolled to improve the ability of the strip 200 to be formed into a roll 300.

Figure 9:
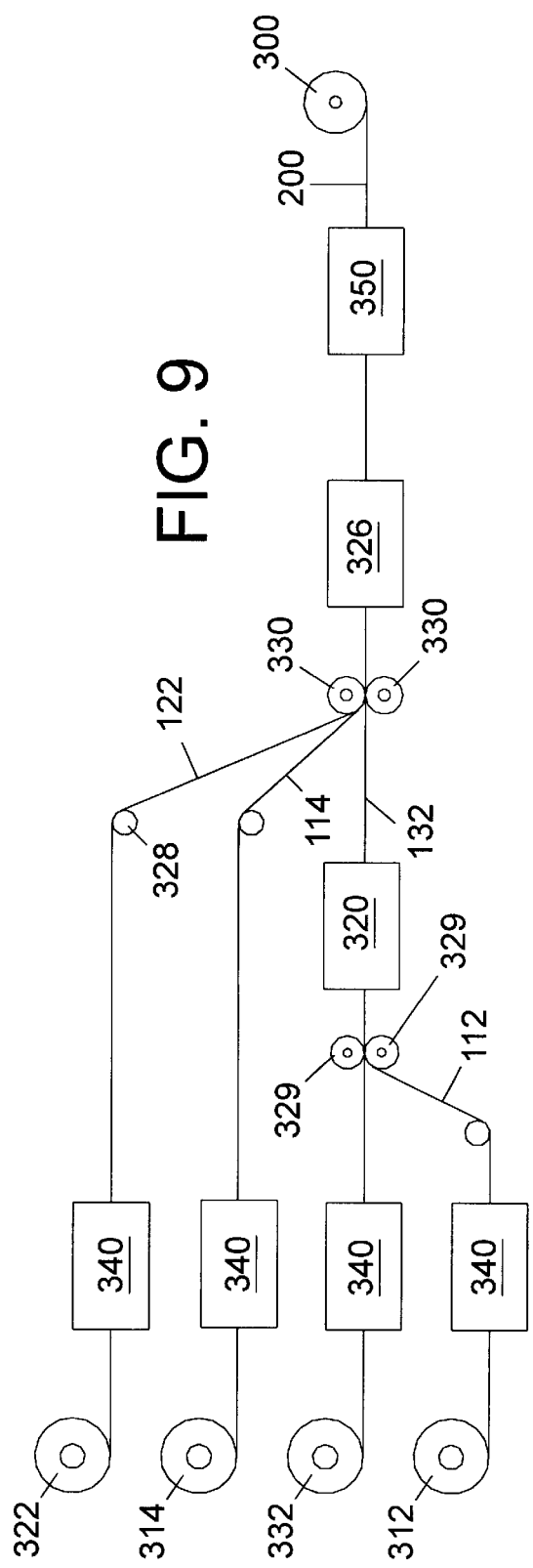
FIG. 9 presents a schematic view of a manufacturing method and apparatus according to an aspect of the invention.

According to a further aspect of the invention, a method of making an electrochemical cell is provided, comprising integrating a base 112, an electrode set 114 on the base 112, and a first reagent 120 (FIGS. 5–7) on the base 112 proximate the electrode set 114, electrode set 14 comprising a plastic strip metallized on opposite sides. Referring now to FIG. 9, a preferred embodiment is presented wherein the integrating is laminating. In the exemplary method presented in FIG. 9, the base 112 is provided as a first rolled sheet or strip 312, and the spacer 132 is provided as a second rolled sheet or strip 332. The two are laminated by passing them through the nip of a pair of opposing first rollers 329. The first reagent 120 is applied in liquid form, and the aperture 136 in the spacer 132 assists in restricting the first reagent 120 to the sample area, at least until the first reagent 120 dries.

The electrode set 114 is provided as a third rolled sheet or strip 314 of plastic metallized on both sides, for example by plating or sputtering. The electrode set 114 is laminated to the base 112 and spacer 132 assembly by passing them through the nip of a pair of second rollers 330.

According to a preferred embodiment, the integrating also comprises a second reagent 126 (FIGS. 5–7) on the base 112, and cover 122 on the base 112. The second reagent 126 is applied by a second application unit 326 after the rollers 330, and the aperture 124 in the cover assists in restricting the second reagent 126 to the sample area, at least until the second reagent 126 dries. The first and second reagents 120 and 126 are preferably superposed with the electrode set 114 in between the two. Both reagents may be applied in liquid form and dried, although other application techniques are envisioned.

One or more stamping and/or slitting stations 340 may be provided ahead of the rollers 330 to create the previously described sample, electrode and connector apertures. Alternatively, the apertures may be pre-stamped. A final stamping and/or slitting station 350 is provided to further shape the strip and/or separate it into individual separated cells.

According to a preferred embodiment the strip is stamped at station 350 to create the legs 140 (FIGS. 5–7). The method preferably concludes with a take-up roll 300 of finished strip 200. Additional apparatus may be provided, such as rollers 328, for further processing or to assist in handling the various materials. Several strips may be processed in parallel, or a single sheet comprising several parallel rows of strips may be formed and subsequently slit into individual strips. Innumerable variations are evident in light of the description provided herein.

The various sheets and strips described herein are formed from an electrically insulating material, such as plastic. Sheets or strips on the order of one to a few thousandths of an inch are particularly preferred. Such materials are sometimes referred to as plastic foil, although thicker materials are also contemplated in the practice of the invention.

The various sheets and/or strips that make up the cell may be bonded together by suitable bonding processes, including heat, ultrasonics, and adhesives. Suitable adhesives include thermoset, thermoplastic, and pressure sensitive, and other adhesives suitable for bonding the layers of an electrochemical cell. The rollers 330 may be heated. Although described in relation to cell 100 for electrochemical analysis, the method may be applied to electrochemical cells having other configurations, such as cell 10 for electrochemical analysis, and similar configurations. Referring again to FIG. 12, adhesive layers 60 may be provided between the cover 22, the spacer 32, and the base 12.

Figure 10:
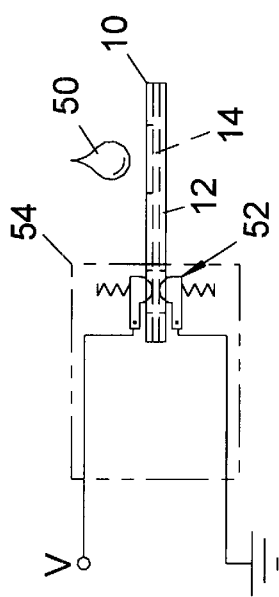
FIG. 10 presents a schematic view of a test method and apparatus according to an aspect of the invention.

Referring now to FIG. 10, an example of a method of analyzing the sample 50 is presented, according to a further aspect of the invention, described with reference to cell 10 for electrochemical analysis. The method comprises contacting the sample 50 with at least a first reagent (as described herein) and the electrode set 14 on the base 12. The method may further comprise applying a voltage across the electrode set 14 and measuring a current, charge, impedance, conductance, potential, or other electrochemically indicated property of the sample 50.

According to a preferred embodiment, at least a second reagent (as described herein) is provided on the base 112, and the method further comprises contacting the sample 50 with the first reagent, the second reagent, and the dual electrode 114.

Potential may be applied to the electrochemical cell of the invention by inserting it into a spring loaded electrical connector 52. The terminals of the connector 52 snap into the connector apertures 28, 30 and 34 of the cell 10. One of the terminals is electrically connected to ground, and the other of the terminals is electrically connected to an electrical potential V thereby forming a closed circuit upon application of the sample 50 to the cell. An analysis device 54 (shown in phantom) is typically provided to measure current, impedance, or other property.

Figure 11:
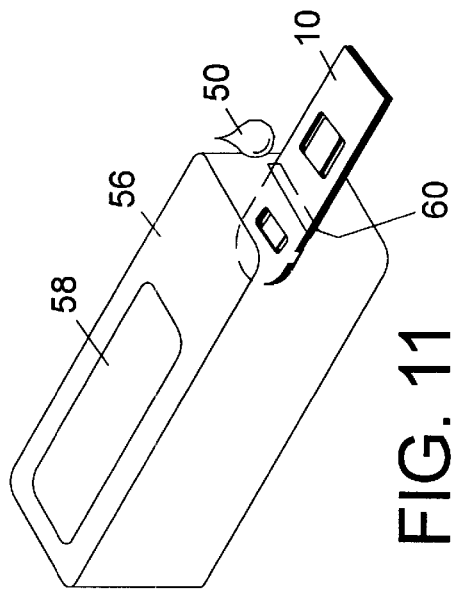
FIG. 11 presents a perspective view of a test method and apparatus according to a further aspect of the invention.

Referring now to FIG. 11, a perspective view is presented of a measuring apparatus 56 that may be used with the electrochemical cell of the invention, for example cell 10 for electrochemical analysis. The measuring apparatus 56 comprises an internal electrical connector and source of electrical potential, such a battery. The measuring apparatus 56 also comprises an internal computing device comprising a microprocessor and memory programmed for analysis. A visual display 58 may also be provided. Analog electronics may also be implemented. The measuring apparatus 56 comprises an opening 60 that receives the terminal end of the cell 10. Examples of measuring apparatus that may be adapted for use with the cells of the present invention are disclosed in U.S. Pat. Nos. 4,963,814; 4,999,632; 4,999,582; and 5,243,516, and U.S. patent application Ser. No. 08/996,280, filed Dec. 22, 1997 to Beaty et al.

Figure 13:
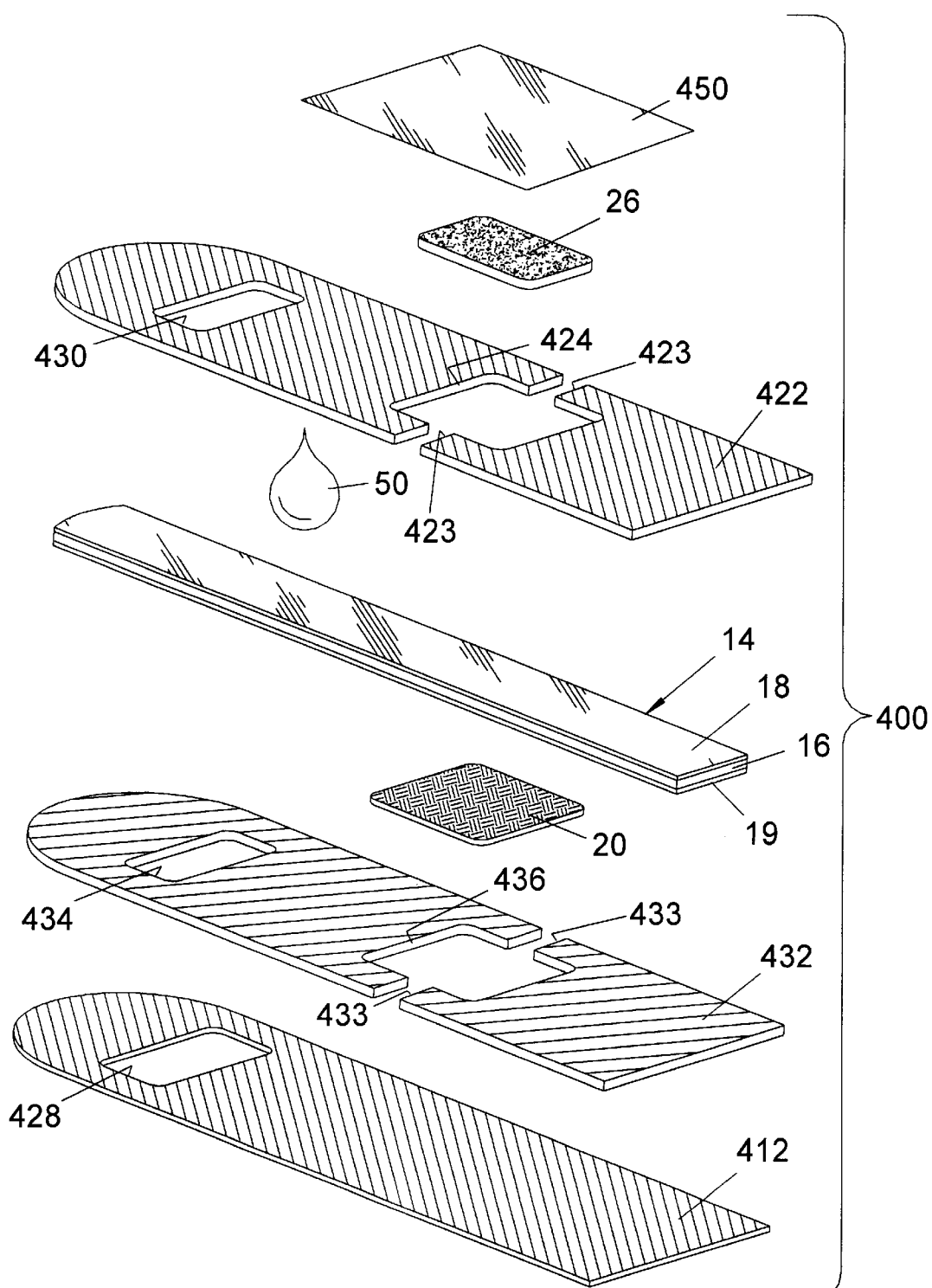
FIG. 13 presents an exploded perspective view of a cell for electrochemical analysis according to a further aspect of the invention.

Referring now to FIG. 13, an exploded perspective view of a cell 400 is presented according to a further aspect of the invention. The cell 400 is very similar to the cell 10 of FIGS. 1–4 and comprises a base 412, a spacer 432 on the base 412, the electrode set 14 on the spacer 432, and a cover 422 on the spacer 432 overlaying the electrode set. The first reagent 20 may be provided on the base 12 proximate the electrode set 14, and the second reagent 26 may also be provided proximate the electrode set 14. The spacer 432 is provided with an aperture 436 and the cover is provided with a corresponding aperture 424. The apertures 436 and 424 form a well that receives the liquid sample 50. The base 412 is provided with an aperture 428, the spacer 432 is provided with a corresponding second aperture 434, and the cover 422 is provided with a corresponding second aperture 430. The apertures 428, 434, and 430 provide access to the electrodes 18 and 19 on either side of the strip 16.

The spacer 432 also comprises an opposing pair of side apertures 433, and the cover comprises an opposing pair of side apertures 423 vertically aligned with the side apertures 433. A window 450 is bonded to the cover 422 overlaying the aperture 424. The window is preferably clear and also covers the apertures 423. The sample 50 is drawn in to the apertures 423 and 433 from the side by capillary action. The opposing apertures 423 and 433 act as a vent. The window is preferably clear, which enables allows a technician administering the test to confirm that the sample 50 is drawn into the well.

Figure 14:
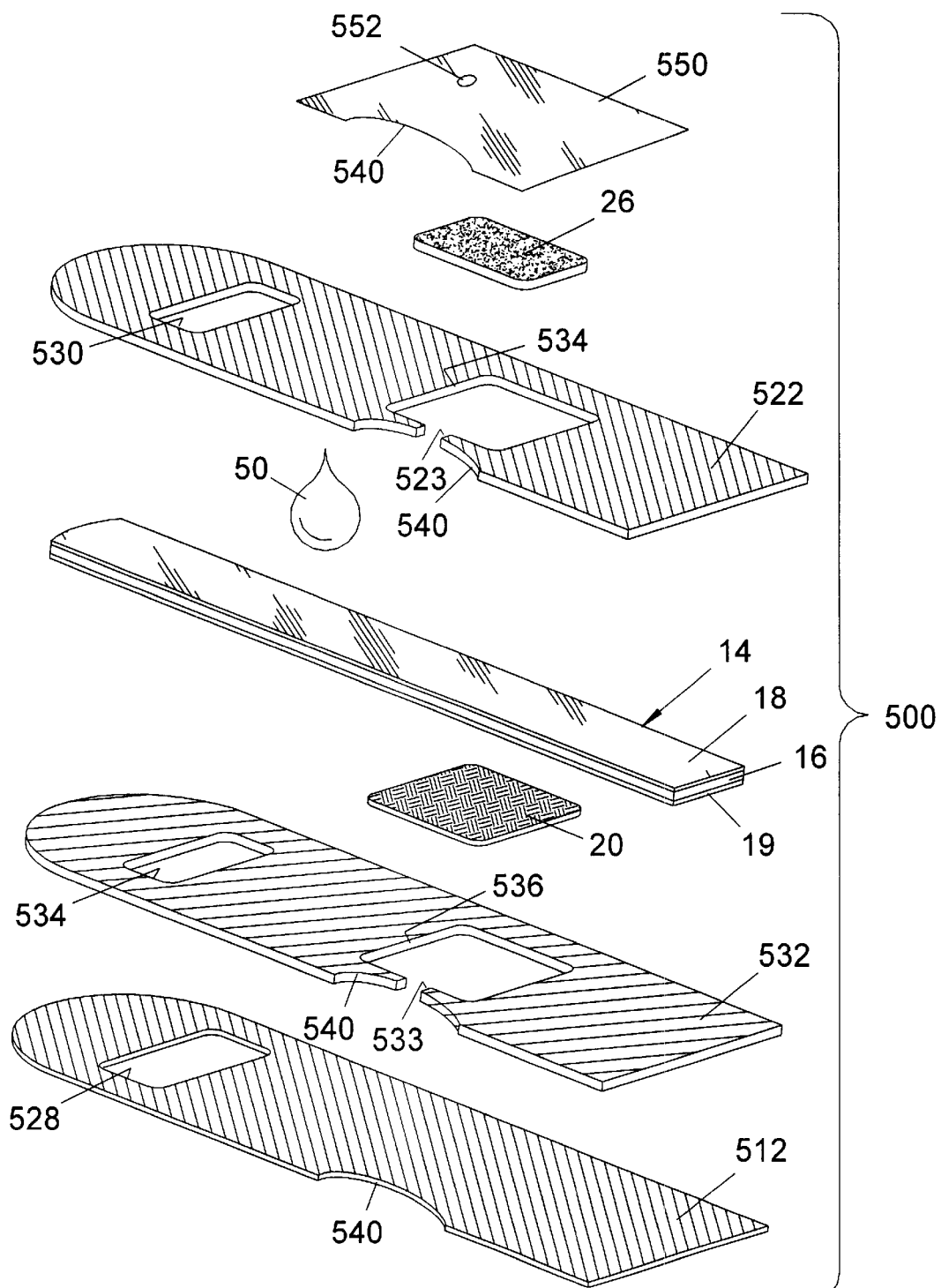
FIG. 14 presents an exploded perspective view of a cell for electrochemical analysis according to a further aspect of the invention.

Referring now to FIG. 14, an exploded perspective view of a cell 500 is presented according to a further aspect of the invention. The cell 500 is very similar to the cell 400 of FIG. 13 and comprises a base 512, a spacer 532 on the base 512, the electrode set 14 on the spacer 532, and a cover 522 on the spacer 532 overlaying the electrode set. The first reagent 20 may be provided on the base 12 proximate the electrode set 14, and a second reagent 26 may also be provided proximate the electrode set 14. The spacer 532 is provided with an aperture 536 and the cover is provided with a corresponding aperture 524. The apertures 536 and 524 form a well that receives the liquid sample 50. The base 512 is provided with an aperture 528, the spacer 532 is provided with a corresponding second aperture 534, and the cover 522 is provided with a corresponding second aperture 530. The apertures 528, 534, and 530 provide access to the electrodes 18 and 19 on either side of the strip 16.

The spacer 532 also comprises a side aperture 533, and the cover comprises a side aperture 523 vertically aligned with the side aperture 533. A window 550 is bonded to the cover 522 overlaying the aperture 524. The window is preferably clear and also covers the side aperture 523. The sample 50 is drawn in to the apertures 523 and 533 from the side by capillary action. The window 550 is provided with a vent 552. The window 550 is preferably clear, which allows a technician administering the test to confirm that the sample 50 is drawn into the well. A curved notch 540 may be provided adjacent the side apertures 523 and 533 to assist in placing the sample in the appropriate location.

The reagents provide electrochemical probes for specific analytes. The choice of specific reagent depends on the specific analyte or analytes to be measured, and are well known to those of ordinary skill in the art. An example of a reagent that may be used in the cell for electrochemical analysis of the present invention is a reagent for measuring glucose from a whole blood sample. A non-limiting example of a reagent for measurement of glucose in a human blood sample contains 62.2 mg polyethylene oxide (mean molecular weight of 100–900 kilodaltons), 3.3 mg NATROSOL 250M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase. This reagent is further described in WO 99/30152, the disclosure of which is incorporated herein by reference.

When hematocrit is to be determined, the reagent includes oxidized and reduced forms of a reversible electroactive compound (potassium hexacyanoferrate (III) ("ferricyanide") and potassium hexacyanoferrate (II) ("ferrocyanide"), respectively), an electrolyte (potassium phosphate butter), and a microcrystalline material (Avicel RC-591F—a blend of 88% microcrystalline cellulose and 12% sodium carboxymethyl-cellulose, available from FMC Corp.). Concentrations of the components within the reagent before drying are as follows: 400 millimolar (mM) ferricyanide, 55 mM ferrocyanide, 400 mM potassium phosphate, and 2.0% (weight: volume) Avicel. A further description of the reagent for a hematocrit assay is found in U.S. Pat. No. 5,385,846, the disclosure of which is incorporated herein by reference. A hematocrit reagent is preferably not deposited on the surface of the electrodes 18 and 19. It may be deposited, for example, on the base 12 beneath the dual electrode set 14.

Other non-limiting examples of enzymes and mediators that may be used in measuring particular analytes in cell 10 of the present invention are listed below in Table 1.

TABLE 1

| Analyte | Enzymes | Mediator (Oxidized Form) | Additional Mediator |
|---|---|---|---|
| Glucose | Glucose Dehydrogenase and Diaphorase | Ferricyanide | |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| HDL Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| Triglycerides | Lipoprotein Lipase, Glycerol Kinase, and Glycerol-3- | Ferricyanide or Phenazine Ethosulfate | Phenazine Methosulfate |

TABLE 1-continued

| Analyte | Enzymes | Mediator (Oxidized Form) | Additional Mediator |
|---|---|---|---|
| | Phosphate Oxidase | | |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | |
| Lactate Dehydrogenase | Diaphorase | Ferricyanide | Phenazine Ethosulfate, or Phenazine Methosulfate |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

In some of the examples shown in Table 1 at least one additional enzyme is used as a reaction catalyst. Also, some of the examples shown in Table 1 may utilize an additional mediator, which facilitates electron transfer to the oxidized form of the mediator. The additional mediator may be provided to the reagent in lesser amount than the oxidized form of the mediator. While the above assays are described, it is appreciated that a variety of electrochemical assays may be conducted with cell 10 in accordance with this disclosure.

According to a preferred embodiment, the reagents are applied in liquid form and dried. As used herein, the term "dry" or "dried" is intended to mean removing water from the reagent to the point where it is immobile, chemically stable, and reactive when it comes in contact with the sample. A liquid reagent may be applied by depositing drops or lines, as an aerosol, or any other suitable process for applying reagents in liquid form. Suitable processes and equipment are available from BioDot, Inc. of California, U.S.A. Completed strips are preferably packaged in sealed containers with desiccants. The sensor strip of the present invention may also include microspheres, as described in pending patent application entitled "MICROSPHERE CONTAINING SENSOR", U.S. patent application Ser. No. 09/471,571 inventors Raghbir Singh Bhullar and Brian S. Hill, filed Dec. 23, 1999, hereby incorporated by reference. The microspheres decrease sample size and improve flow of the sample within the cell. A reagent may be deposited on the microspheres.

Referring again to FIGS. 1 and 12, in one embodiment, the base 12 may be formed from polyester on the order of 125 micrometers thick, the spacer may be formed from polyester on the order of 50 micrometers thick, and the cover may be formed from polyester on the order of 75 micrometers thick. The adhesive layers 60 may be a polyacrylate pressure sensitive adhesive on the order of 25 micrometers thick. The electrode set 14 may be formed from the UPILEX brand polyimide from Ube, Japan, which is available precoated with gold, palladium or platinum from TECHNI-MET of Connecticut; or ULTEM 1000 (polyetherimide) from GE, available coated with copper. The metal coating may be on the order of 50 nanometers thick.

Referring again to FIG. 5, in one embodiment, the cell 100 is formed from similar materials, preferably thinner to decrease overall thickness thereby increasing flexibility for further processing into roll 300 or fan-fold stack 400. For example, the base 112, spacer 132, and cover 122 may be formed from polyester 50 micrometers thick. The electrode set 114 may be formed from materials as just described in relation to electrode set 14. Pressure sensitive adhesive layers on the order of 25 micrometers may implemented to bond the various layers. However, strip 100 that is coiled will be subjected to greater stress during packaging, and may even be stored in a stressed state. Therefore, a thermoset adhesive may be desirable, which may decrease interlaminar creep during storage. A thermoset adhesive may also be thinner, which contributes to an overall minimized thickness.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

What is claimed is:

1. A cell for electrochemical analysis of a liquid sample, comprising:
   a base;
   a spacer overlaying said base;
   a dielectric strip overlaying said base and said spacer, said dielectric strip having opposing first and second surfaces;
   a first electrical conductor on said first surface that defines a first sensing region;
   a second electrical conductor on said second surface that defines a second sensing region opposite said first sensing region; and
   a cover overlaying said dielectric strip, said spacer and said cover having respective apertures, said apertures aligned to define a well for receiving said liquid sample.

2. The cell of claim 1 further comprising a plurality of said cells connected in seriatim.

3. The cell of claim 1 further comprising a first reagent proximate said first and second sensing regions.

4. The cell of claim 3 further comprising a second reagent proximate said first and second sensing regions.

5. The cell of claim 1 further comprising:
   a first reagent proximate said first sensing region; and
   a second reagent proximate said second sensing region;
   wherein said dielectric strip, said first electrical conductor, and said second electrical conductor are disposed between said first and second reagents.

6. The cell of claim 1 wherein said base comprises an aperture for an electrical connector and said cover comprises an aperture for an electrical connector, said first and second electrical conductors being accessible through said apertures.

7. The cell of claim 6 wherein said apertures are superposed.

8. A cell for electrochemical analysis of a liquid sample, comprising:
   a base;
   a spacer overlaying said base;
   a dielectric strip overlaying said base and said spacer, said dielectric strip having opposing first and second surfaces;

a first electrical conductor on said first surface;

a second electrical conductor on said second surface;

wherein said first electrical conductor does not extend beyond said first surface, and said second electrical conductor does not extend beyond said second surface; and a cover overlaying said dielectric strip, said spacer and said cover having respective side apertures, said side apertures being vertically aligned so that said liquid sample is drawn into said cell through said apertures.

9. The cell of claim 8 further comprising a plurality of said cells connected in seriatim.

10. The cell of claim 8 wherein said cell comprises a first reagent proximate said first electrical conductor.

11. The cell of claim 10 wherein said cell comprises a second reagent proximate said second electrical conductor.

12. The cell of claim 8 further comprising:

a first reagent proximate said first sensing region; and a second reagent proximate said second sensing region;

wherein said dielectric strip, said first electrical conductor, and said second electrical conductor are disposed between said first and second reagents.

13. The cell of claim 8 further comprising a spacer on said base, said dielectric strip being on said spacer.

14. The cell of claim 8 further comprising a spacer on said base, said spacer having an aperture over said first and second electrical conductors, said cover having an aperture over said aperture in said spacer, both said apertures being over said gap.

* * * * *